United States Patent [19]

Steinemann

[11] Patent Number: 4,983,184
[45] Date of Patent: Jan. 8, 1991

[54] ALLOPLASTIC MATERIAL FOR PRODUCING AN ARTIFICIAL SOFT TISSUE COMPONENT AND/OR FOR REINFORCING A NATURAL SOFT TISSUE COMPONENT

[75] Inventor: Samuel G. Steinemann, St. Sulpice, Switzerland

[73] Assignee: Institut Straumann AG, Waldenburg, Switzerland

[21] Appl. No.: 254,366

[22] Filed: Oct. 5, 1988

[30] Foreign Application Priority Data

Oct. 16, 1987 [CH] Switzerland .......................... 4081/87

[51] Int. Cl.$^5$ .......................... A61F 2/02; A61F 2/08
[52] U.S. Cl. ........................................ 623/66; 623/11; 623/13
[58] Field of Search .................. 623/13, 16, 11, 66; 87/7, 8

[56] References Cited

U.S. PATENT DOCUMENTS

| | | | |
|---|---|---|---|
| 4,089,071 | 5/1978 | Kalnberz et al. | 623/16 |
| 4,345,339 | 8/1982 | Müller et al. | 623/13 |
| 4,693,721 | 9/1987 | Ducheyne | 623/66 X |
| 4,728,329 | 3/1988 | Mansat | 623/13 |
| 4,741,087 | 5/1988 | Plummer, Jr. | 87/7 X |
| 4,777,859 | 10/1988 | Plummer, Jr. | 87/7 |
| 4,778,468 | 10/1988 | Hunt et al. | 623/16 |

OTHER PUBLICATIONS

"Animal Experiments for Comparison of Various Alloplastics Materials in Ligament Replacements", L. Clases et al., Nov. 13, 1984.

*Primary Examiner*—Alan W. Cannon
*Attorney, Agent, or Firm*—Toren, McGeady & Associates

[57] ABSTRACT

The alloplastic material comprises bundles of metallic fibers loosely held together. The fibers preferably consist of a titanium-based alloy containing at least one of the metals niobium, tantalum, zirconium, chromium, molybdenum and aluminum, and may be provided with a coat of an organic substance selected to be absorbed inside a human or animal body. On the outer surfaces of the fibers consisting of the named alloy there may arise layers of oxides effective to protect the metal beneath against chemical influences taking place in the body. Moreover, the metals present in the fibers in the form of alloy components are not toxic and enable a good bond with natural tissue to take place. Without the optional coat, the fiber thickness has a value of less than 20 micrometers and preferably 15 micrometers or less. Thus, subjecting the fibers to bending, as takes place with alloplastic material inside the body, will not cause any fatigue fractures.

32 Claims, 2 Drawing Sheets

U.S. Patent Jan. 8, 1991 Sheet 2 of 2 4,983,184
Fig. 3
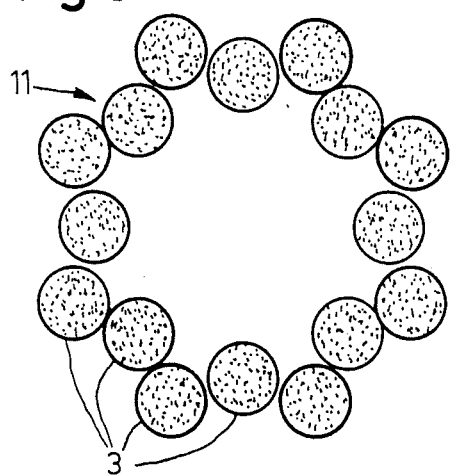
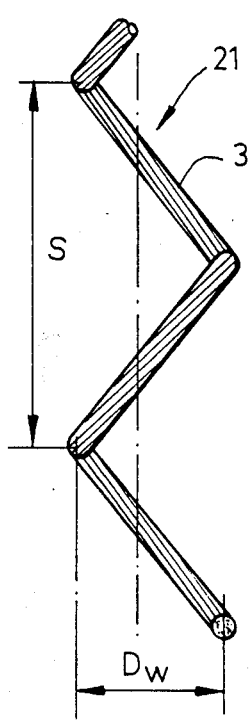
Fig. 4
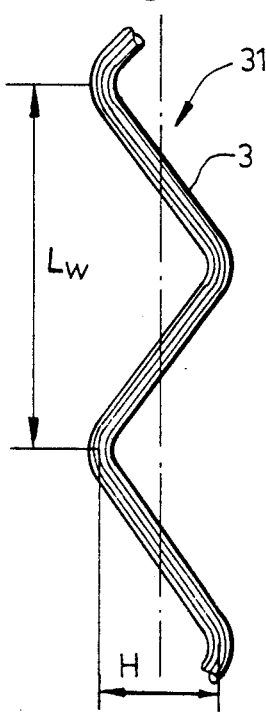
Fig. 5

ALLOPLASTIC MATERIAL FOR PRODUCING AN ARTIFICIAL SOFT TISSUE COMPONENT AND/OR FOR REINFORCING A NATURAL SOFT TISSUE COMPONENT

BACKGROUND OF THE INVENTION

1. Field of the Invention

The present invention concerns an alloplastic material for producing an artificial soft tissue component and/or for reinforcing a natural soft tissue component, for example a ligament, a tendon or a supporting tissue of a human or animal body.

The alloplastic material may be used in medicine and surgery, and be implanted into a human or animal body. In the following the term 'body' will frequently be used to mean 'human or animal body'. Similarly, the term 'bundles' referring to components of the alloplastic material, will frequently be used to mean 'one or more bundles'. The invention equally concerns a method for producing the alloplastic material of the invention.

2. The State of the Art

Artificial ligaments and tendons made of bundles interwoven or plaited, and consisting of plastic fibers or of carbon fibers coated with a substance absorbable inside the body are known in the art. The plastic fibers used for the purpose have been of thicknesses between 20 and 30 micrometers, whereas the carbon fibers used have been from 7 to 8 micrometers thick. Attention is called in this connection to the article titled "Implantatmaterialien für den alloplatischen Bandersatz" by L. Claes, C. Burri and R. Neugebauer, which appeared in the 5th Series of Lectures of the Work Committee for Implants (5.Vortragsreihe des Arbeitskreises Implantate) dated Nov. 13, 1984, page 193 of the Deutscher Verband für die Materialprüfung e.v. Fibers made of plastic materials are subject, however, to strong aging effects within the body, probably caused, at least in part, by their absorbing water from body fluids. As time goes on, the plastic fibers may undergo the phenomenon known as creep, involving a slow change in length, a reduction in strength or mechanical resistance, and brittleness. The mechanical properties of carbon fibers used at present predominantly for implants are strongly non-isotropic, due to the graphitic structure of carbon. Bending loads or stresses with small radii of curvature, or even relatively slight shearing stresses, may cause fibers to fracture. This is confirmed by the cited publication of Claes et al. Furthermore, carbon fibers have only low ductility and tend to crumble, particularly if their coats have been dissolved after a longer stay inside the body.

SUMMARY OF THE INVENTION

It should therefore be apparent, that the art is still in need of an alloplastic material for producing an artificial soft tissue component and/or for reinforcing a natural soft tissue component, as well as of a method for producing the alloplastic material, which are not associated with the aforementioned drawbacks and limitations of the state-of-the-art proposals.

It is therefore a primary object of the invention, to provide a novel alloplastic material for making an artificial soft tissue component and/or for reinforcing a natural soft tissue component, for example a ligament, a tendon or a supporting tissue of a human or animal body, as well as a method for producing the alloplastic material, which is not associated with the drawbacks and limitations of the prior art as heretofore discussed and which effectively and reliably fulfills an existing need in the art.

Another and more specific object of the invention is to provide a novel alloplastic material which is to avoid the disadvantages of known materials and which, in particular, is capable of resisting bending stresses resulting from bending to small radii of curvature as well as relatively large shear stresses, and which is able to preserve its mechanical strength and flexibility even if it remains in a human or animal body for a relatively long duration.

The foregoing and other objects are attained in accordance with some aspects of the invention by providing an alloplastic material which comprises fibers of a thickness less than 20 micrometers containing a metallic material.

Further objects of the invention are attained by providing a method for producing an alloplastic material comprising steps in which a number of wires corresponding to the number of wires to be formed are embedded into a matrix consisting of a metallic material different from the metallic material of the fiber, the wires together with the matrix are made longer and thinner by deformation and subsequently the matrix is dissolved by means of an acid to yield a bundle of fibers.

A few advantages of the invention will be described in the following.

The alloplastic material may comprise one or more bundles or, by preference, two or more bundles of fibers. One such bundle may contain a number of fibers within the range of 200 to 1000, or even up to 3000.

The fibers belonging to one bundle should be preferably held together loosely, in the relaxed state of the alloplastic material not yet implanted into the body, to generally have clearance spaces between adjacent fibers. The term 'generally' is meant to imply, that fibers, at least at longitudinal sections, having sums amounting to a substantial part, such as more than 60%, and preferably 80% of the entire fiber length, are separated from the nearest neighbouring fiber by a clearance space. However, at some places, for example at places at which the bundles are bent to small radii of curvature, as at the longitudinal edges of a plaited ribbon, the fibers may touch each other in pairs or groups. As an alternative, the fibers of a bundle may run parallel to the longitudinal axis of the bundle or be wound around this axis. In the latter case, the pitch of the fibers in the bundle may be equal to from 5 to 10 times, or more, the diameter of the bundle.

In preferred embodiments of the alloplastic material, the fibers have a plane zigzag- and/or wave-shape, and/or a 3-dimensional helix-shape. If a single fiber bundle is involved, this bundle may be zigzag-, wave-,or helix-shaped. If, as is generally the case, two or more fiber bundles are provided, for example from 8 to 20, then the bundles may be mutually connected, in a loose manner, by plaiting, knitting, weaving or twisting. As an alternative, several types of connections may be combined with each other. These methods of connection may lend the bundles their zigzag-, wave-, or helix-shapes, while mutually supporting each other along their entire length, in regular intervals or without interruptions. Instead, two or more bundles may run zigzag-, wave-, or helix-shaped adjacent to each other, along parallel axes, and be fastened at their ends to common fastening members, but for the rest unconnected.

The alloplastic material may have an elongated shape, a shape suited for making an artificial tendon or an artificial ligament. If it possesses a defined longitudinal direction, then the alloplastic material may have to advantage the central axis of the zigzag- or wave-line, or the helix formed by respective bundles to run parallel to the defined longitudinal direction. In this way, at least the bundle sections forming, in regards to length the largest part of each fiber bundle, will form an angle with this longitudinal direction. It is of course possible, to produce areal fiber formations, that do not necessarily have a defined longitudinal direction, but rather a contour of polygonal or roundly shape, suited for making pieces of a supportive tissue, such as the diaphragm, or pieces of a membrane, or pieces of an inner or of an outer skin or membrane.

The fibers or, if they are provided with a non-metallic case, their cores, comprise a metallic material with at least one metal, and, in a preferred embodiment, may consist of an alloy, which, in addition to titanium as base metal, also contains one or more of the metels niobium, tantalum, zironium, chromium, molybdenum, iron and aluminum. The percentage by weight of titanium in the alloy should be the largest, and generally have a value of 50% or more. Furthermore, not considering any impurities that might be present, the fibers should preferably not contain any other metals than titanium and the alloy components mentioned before.

Titanium is reactive toward oxygen. Thus, if a fiber consisting of a titanium alloy is placed into an oxidizing environment containing free or bound oxygen, where it subjected to the action of oxygen from the air or from the inside of a human or animal body, such as oxygen present in electrolytic body fluids, then a compact filmlike metal oxide layer, specifically $TiO_2$, if the fiber contains titanium, will be generated on the outside surface of the fiber. An oxide layer of this kind provides good protection against corrosion to the metal underneath. The protection of the oxide layer is effective against chemical influences too, which may come from the fluids and other natural substances of a body and act upon an alloplastic material implanted into such a body. Investigations carried out on titanium parts implanted into the body have shown, that the oxidation reaction is very slow and proceeds even in a layer close to the metallic surface at a rate of oxidation of about $2 \times 10^{-5}$ micrometers/day only. Thus, based upon the aforementioned rate of oxidation, the degradation require a least 50,000 days i.e. at least 137 years to accomplish the removal of 1 $\mu$m. The actual time required for the oxidation is, however, substantially longer, because the surface layer of oxide protects the metal underneath against corrosive effects, and specifically against oxidation too, and thus slows down the progress of the oxidation. Therefore, with a typical diameter of the fibers of 10 to 15 $\mu$m the degradation by oxidation will have practically no effect. A similar situation exists in regards to the possible alloy components niobium, tantalum, chromium and aluminum, which are similarly reactive with respect to oxygen. Iron, also a possible alloy component, is corrosion-resistant, at least as a component of titanium-based alloy. Moreover, titanium and the aforementioned alloy metals show no toxic effects when implanted into the body. Thus, titanium and the titanium-based alloys are biologically inert and not toxic, and correspondingly produce no tissue reactions. Moreover, the surface metal oxide layer is effective to electrically insulate the metal below against the bodily tissue.

Titanium and the named titanium alloys also have good mechanical strength and a comparatively low modulus of elasticity. This latter property is of particular advantage, because it keeps stresses resulting from bending loads low. Titanium belongs to the metals of the alpha-type. Titanium alloys have various phase structures, depending on their compositions, and correspondingly belong to the alpha-type, the alpha-beta-type, or the beta-type. The TiNbTaAl-alloy containing 3% by weight niobium, 1% by weight tantalum, 6% by weight aluminum and the rest titanium, belongs for example to the alpha-type. Other alloys of the alpha-beta-type include for example the TiAlFe-alloy containing 5% by weight aluminum, 2.5% by weight iron and the rest titanium, and the TiNbAl-alloy containing 7% by weight niobium, 6% by weight aluminum and the rest titanium. Alloys of the beta-type are the TiNb-alloy containing 40% by weight niobium and the rest titanium, and the TiMoZrAl-alloy containing 15% by weight molybdenum, 5% by weight zirconium, 3% by weight aluminum and the rest titanium. The modulus of elasticity typically lies at 100 to 120 GPa for titanium, the alloys of the alpha-type and of the alpha-beta-type, and at about 65 to 110 GPa for the alloys of the beta-type, the exact values being dependent upon the heat treatment applied. The alloys of the beta-type have a cubic structure and as a feature shared to some extent by the alloys of the alpha-beta-type they display larger plastic deformability than titanium and than the alloys of the alpha-type having hexagonal structure. In consequence, the alloys of the alpha-beta-type and, above all those of the beta-type display more advantages than the materials of the alpha-type. Moreover, the mechanical strength of the alloys of the beta-type may be increased by heat treatment such as annealing, in particular solution annealing, and/or aging.

Subsequent to having been made, the metallic fibers display a relatively rough surface. This rough surface structure makes a good adherence of the bodily tissue possible, which tissue grows interpenetratingly into the alloplastic material implanted into the body. The interpenetrating growth of the connecting tissue may be improved, however, by the additional measures of enclosing the metallic formation and/or the bundles consisting of this formation and/or the formation consisting of the totality of several bundles, into an organic substance that may be absorbed inside the body, specifically, by the body fluids. Organic substances suited for this purpose, and which may be absorbed by the body within a few days are collagen, polyglactin, polylactate and gelatin.

The fibers should not be stressed beyond the elastic limit even if an alloplastic material containing the fibers runs over a sharp edge inside the body, or is strongly bent for other reasons. It was found that this condition can be fulfilled, by keeping the value of the so-called critical radius of curvature $r_c$ at less than 1 mm, and by preference at less than or approximately at 0.5 mm. In this context, the term critical radius of curvature $r_c$ is meant to refer to the smallest radius of curvature, to which the fibers may be bent, without any fracture occurring. If the fibers are circular in cross-section and are of diameter d, and if the fiber material has a modulus of elasticity E and a maximum allowable tension stress $\sigma_z$, it can be shown, that the critical radius of curvature may be expressed by the formula:

$$r_c = \frac{Ed}{2\sigma_z} \qquad (1)$$

For cold-formed titanium, for example, the allowable tension stress has a value $\sigma_z = 0.9$ GPa and the modulus of elasticity a value of $E = 105$ GPa. For a cold-formed TiNb-alloy containing the percentages by weight specified before, the corresponding values are $\sigma_z = 0.88$ GPa and $E = 69$ GPa. If a critical radius of curvature of 0.5 mm is assumed, there results for titanium a fiber diameter of about 9 micrometers and for the named TiNb-alloy a fiber diameter of about 13 micrometers. If the maximum allowable tension stress is replaced in formula (1) by the lower allowable fatigue stress corresponding to repeated application of bending loads, then the corresponding fiber diameters must be further reduced by about 40%.

If the fibers are circular in cross-section, their thickness, i.e. their diameter, should be in the range of at least 5 and less than 20 micrometers. If the fibers are coated with an organic substance, the specified fiber thickness is meant to refer to the thickness in the uncoated state, i.e. the thickness of the metallic cores of the fibers. Rather than having the preferred circular cross-section, the fibers may have, as an alternative, a different, roundly cross-sectional shape, that deviates more or less from the circular cross-section. In such a case, the fiber thickness is meant to refer to the maximum cross-sectional dimension of the uncoated fiber.

If the alloplastic material is implanted into the body, then the loose structure of the material will enable the body fluids to penetrate between the fibers and to make natural body tissue interpenetratingly grow between the fibers. If the fibers consist of titanium or of a titanium-containing alloy, then $TiO_2$ will be generated on the outer surfaces of the fibers, as described before. Hydroxide ions, radicals with a hydroxyl-group and radicals with an amino-group can readily deposit on these outer surfaces. Titanium and its named alloys therefore display bioactive behaviour. This is intended to mean, that after the alloplastic material has been implanted into the body, the titanium and its alloys will enable and encourage an intimate bond between the fibers and the natural, soft tissue and perhaps the solid bone substance. There will result, so to speak, a composite material consisting of alloplastic material and of natural tissue, the latter assuming the function of a matrix. If, in spite of the good pliability of the fibers, one individual fiber of the alloplastic material should break, then the natural soft tissue that fixedly adheres to the respective fiber will be able, by itself, to transmit the force onto the neighbouring fibers and, evidently, to bridge over the place of fracture. The force of adhesion by which the natural body tissue fixedly adheres to the outer surface of the fibers, is equal to the product of the outer surface of the fiber times the adhesive stress $\sigma_h$. By defining the critical shearing and tear-out length L as a specific length of a section of a fiber, at which the adhesive force is equal to the fracture stress of the fiber, said length L may be expressed as $$L = \frac{d\sigma_z}{4\sigma_h} \qquad (2)$$

Experimental tests referring to the adhesion of bones to rough titanium surfaces, yielded adhesive stresses of 3 MPa. Assuming that the adhesive stress for soft tissues has about the same value, there results for titanium fibers of a diameter of 13 micrometers, a critical tear-out length of about 1 mm, or slightly less. If, as mentioned before, the fiber diameter d has a value less than 20 micrometers and, for example, between 5 and 15 micrometers, it is possible to obtain, on the one hand, a sufficiently small critical radius of curvature, and on the other hand, a tear-out length L clearly larger than the distance between adjacent fibers in a bundle of fibers loosely held together. This last feature contributes, should a fracture of an individual fiber take place, to a good transmission of force from the fractured fiber onto the adjacent fibers.

If natural, human or animal tissues, such as ligaments, fasciae, and tendons are stretched to the point of fracture and the applied tension force is plotted as a curve, then the slope of the curve will increase at the beginning and remain constant thereafter, until the curve flattens out and subsequent to reaching the ultimate tension stress, i.e. the maximum tension force before fracture, it will slightly fall off. On the other hand, if an individual metallic fiber is stretched, the corresponding curve will rise linearly from the beginning, until the region of plastic deformation is reached and the slope of the curve will slightly decrease, but will remain positive until fracture occurs. Irrespective of these different forms of the curve, the mechanical strength and elongation properties of the metallic fibers strongly differ, quantitatively too, from the corresponding properties of natural tissues. Whereas the modulus of elasticity of natural tissues, tendons and ligaments, lies in the range of 0.5 to 1.8 GPa in the linear portion of the curve, the modulus of elasticity of the fibers of titanium has a value of 105 GPa, as already mentioned, and it lies between 65 and 120 GPa for the titanium alloys of the mentioned types. The maximum allowable tension stress has a value between 60 and 110 MPa for the named natural tissues, a value of 800 MPa for pure titanium, and a value between 800 and 1400 MPa for titanium alloys. Significant is, however, that natural, soft tissues of the mentioned kind may be typically stretched in the elastic region of deformation about 10%, and about 15% to fracture, whereas metallic fibers can only be stretched about 1% in the elastic region of deformation.

However, the fibers may be loosely interconnected in the way mentioned before and arranged to follow a zigzag-, wave-, and/or helix-shaped course. In the case of an alloplastic material comprising for example a defined longitudinal direction and serving for example for making a tendon or the like, the fibers may run at least generally obliquely to this longitudinal direction, and thus to the direction along which the alloplastic material is meant to transmit a tension force while in use. In the case of an areal alloplastic material destined to be made into a diaphragm, the fibers thereof may be arranged to run, at least in certain places, obliquely to the direction along which a tension force is to be transmitted while the alloplastic material is in use. The individual fibers will then be able to move relative to each other, during the deformation of the alloplastic material, to a limited degree. The alloplastic material will thus obtain a certain elasticity of form. This elasticity of form will be considerably increased after the alloplastic material has been inserted into the body, due to the fact that natural soft tissue, such as connecting tissue, will interpenetrate the clearance spaces between the fibers. By suitable design, one may achieve to have the alloplastic material, starting out from its relaxed state while changing the course of the fibers, stretched at least after it has been interpenetrated by natural tissue at least in one direction, by 5% or more, or even by 10 to 20%, without causing the fibers to undergo any plastic deformation worth mentioning, and evidently without any fiber fracture.

If the alloplastic material implanted into the body has been grown into or interpenetrated by natural tissue, there will form a composite material, the forces exerted onto this material being taken up in part by the metallic fibers, and in part by the natural tissue. In this case, the effective modulus of elasticity, at least in the initial phase of a stretching process, will be equal to the weighted average between the modulus of elasticity of the alloplatic material and the modulus of elasticity of the natural tissue, the weighting factors used for computing this weighted average being proportional to the share of the sum of the fiber cross-sectional areas and the share of the sum of the soft tissue cross-sectional areas in the total cross-sectional area of the composite material. Moreover, the loose structure of the alloplastic material makes it possible, to have the tension forces acting upon it be distributed relatively uniformly over many fibers. It is only when the form-elastic elongation of the composite material has been exhausted that the fibers themselves will begin to stretch to any extent worth mentioning, whereby then the modulus of elasticity will become larger. Thus, even though the metallic fibers and the natural tissue strongly differ from each other in regards to mechanical strength and deformation properties, it is nevertheless possible to use metallic fibers for making an alloplastic material, which, as a whole, particularly after it has been grown into or interpenetrated by natural, soft tissue, will yield a qualitatively similar relationship between tension stress and elongation, as the corresponding relationship of the originally provided natural tissue.

When making a strap- or hose-shaped plait, the plaiting angle, i.e. the angle between a fiber bundle and the longitudinal direction of the plait may, if a form-elastic extensibility of at least 10% is to be realized, have a value between 30° and 60° or, for example, between 40° and 50°, depending upon the density and the degree of space filling of the plait. If the alloplastic material comprises one single fiber bundle running zigzag- or wave-shaped within a plane, or several fiber bundles having such shape and running, at least to some extent, freely next to each other, and if a form-elastic extensibility of 5% to 10% or more is desired, then the ratio between the wave length and the wave height may have a value of about 4, or less. If one or each fiber bundle is by itself helix-shaped, then the ratio between pitch and diameter of the helix for achieving extensibility of 5 to 10% or more, may be for example of the order of magnitude of 6 or less.

It is possible, by mathematical analysis, to estimate the manner in which, in a composite material which consists of metallic fibres and of natural tissue that fills in the clearance spaces between the metallic fibers, the forces become distributed over the fibers and the natural tissue, as well as the kinds of forces that the fibers and the tissue are able to take up before fracture. These analyses show, that the natural tissue, if its share in the total volume of the composite material reaches a value between 90 and 99%, will take up at least the same share of the total force as will the fibers, and can take up at least a similar maximum force before fracture, as the fibers. This means that, for example, after implanting an alloplastic material to serve as an artificial ligament, so much material may interpenetratingly grow into the implanted ligament, that a new ligament consisting of natural tissue will arise, within which the alloplastic material will merely serve as guide frame for the interpenetrating tissue.

The total cross-sectional area of a fiber bundle and the ratio V between the sum of the cross-sectional areas of the fibers belonging to the same bundle and the total cross-sectional area of the bundle, may vary along the bundle. If, for fulfilling its intended role, an elongated, alloplastic material comprising one or several fiber bundles, is fastened at its ends onto parts of the body, then the fibers at these ends will evidently be additionally pressed together at the fastening places. Furthermore, the fibers may also become pulled together, if the alloplastic material, while used as artificial ligament or tendon is subjected to tension stress. If, subsequent to being implanted into the body, the alloplastic material is interpenetratingly grown into by natural tissue, the material may become deformed by this growing-in tissue, causing its total cross-sectional area to increase, for example. Even though the distances between adjacent fibers after the implantation will not be the same as those before implantation, the ratio between the total volume of the fibers and the total volume of the grown-in tissue, resulting after the natural tissue has grown into place, will still be largely influenced by the distances between fibers in the relaxed unstressed alloplastic material before implantation. In order to enable the alloplastic material to be sufficiently interpenetrated and grown into by natural tissue, it is likely to be of advantage to have the ratio V for the material, in relaxed state and before implantation, be not more than 0.5, by preference not more than 0.2 and for example not more than 0.1 or 0.01. These limit values should preferably be valid for the average value of the ratio V also, the term average value being meant to refer to the value of the ratio V averaged over the entire length of the fiber bundle of the relaxed and unfastened alloplastic material.

Metallic fibers having diameters less than 20 micrometers cannot be produced by methods used for manufacturing individual wires. Such fibers may, however, be produced in bundles, by inserting comparatively thick wires of preferably circular cross-section, in a number corresponding to the desired number of fibers in a bundle, and consisting of the same material as the material of the fibers to be made, into bores of a block consisting of a different metallic material than the fibers. The material of the block effective to function as a matrix, is to preferably be softer than the material of the fibers and to have a similar ductility in regards to elongation-deformations, as the material of the fibers. The matrix may consist for example of copper or of a copper-nickel alloy. The composite blank consisting of the matrix and the wires imbedded thereinto, may be stretched and reduced in diameter, in steps, by hot and/or cold deformation processes, such as pressing and/or rolling and/or drawing, to make the thickness of the wires decrease to the desired thickness of the fibers. At least the terminal part, or terminal phase, of the deformation process shall consist by preference of a cold forming process. The deformation may be carried out by hot-pressing and subsequent cold-drawing. In a deformation process of this kind effecting a reduction in the cross-section as well as a lengthening of the rough blank and of the wires, the volume of the blank and of the individual wires remains preserved. A similar method of deformation is known to be used in the manufacture of superconductors, in which fibers of a titanium-niobium-alloy are imbedded into a copper matrix. Whereas in the completed superconductors the matrix remains preserved as a component, when manufacturing fibers for an alloplastic material the matrix is dissolved after deformation, by means of an acid, such as nitric acid, not reacting with the fiber material.

As already explained, each fiber bundle of the completed alloplastic material should preferably be formed to follow a zigzag-, wave-, and/or helix-shaped course, while several bundles may be united to yield a plaited, knit or woven formation and/or a hose and/or a rope or a yarn. Such a shape of the fiber bundles may be implemented by means of a form-giving process, in which the fibers are subjected essentially to bending only and are not made any thinner or longer, or at least not significantly so, in contrast to the deformation they previously underwent, while they were being produced of wires. During this form-giving process, which takes place without any substantial reduction in cross-sectional area or elongation of the fibers, the fiber bundles may be twisted and/or, depending on the desire type of alloplastic material to be produced, formed as individual bundles zigzag-, wave-, or helix-shaped, and/or connected with other fiber bundles, in advance of dissolving the matrix, together with the same, or after matrix dissolution. If the twisting and/or plaiting and/or other formgiving of the fiber bundle is carried out before the dissolution of the matrix, then the rigid connection between the fibers and the matrix will guarantee that the fibers will be bent in the same way the matrix that surrounds them is bent, without breaking. The ductility and/or mechanical strength of the fibers may be additionally influenced in desired manner by heat treatment, such as annealing, for example soft annealing or solution annealing, and/or by aging. This heat treatment may be carried out after the fibers have been manufactured in a volume preserving and elongating reduction in cross-section, specifically before and/or concurrently with and/or subsequent to the dissolution of the matrix, as well as before and/or concurrently with and/or subsequent to the form-giving of fibers carried out, in the described manner, without any substantial elongation and reduction in cross-section. If the fibers consist for example of a titanium alloy of the beta-type, and particularly if, in addition, in the course of a multi-stepped deformation process serving for the manufacture of fibers by elongation and reduction in cross-section, a cold forming process is applied, at least in the terminal phase, then the strength of the fibers may be additionally increased by heat treatment, such as by solution annealing and/or aging. Furthermore, the fibers may be coated by means of one of the named organic substances. This coating-step may be carried out either subsequent to producing a fiber bundle, or only after the bundle has been formed to zigzag-, wave-, or helix-shape, and/or connected with other fiber bundles, but evidently after the matrix has been dissolved.

BRIEF DESCRIPTION OF THE DRAWINGS

The subject matter of the invention shall now be explained by making reference to embodiments shown in the drawing. There show.

DETAILED DESCRIPTION OF THE PREFERRED EMBODIMENTS

Figure 1:
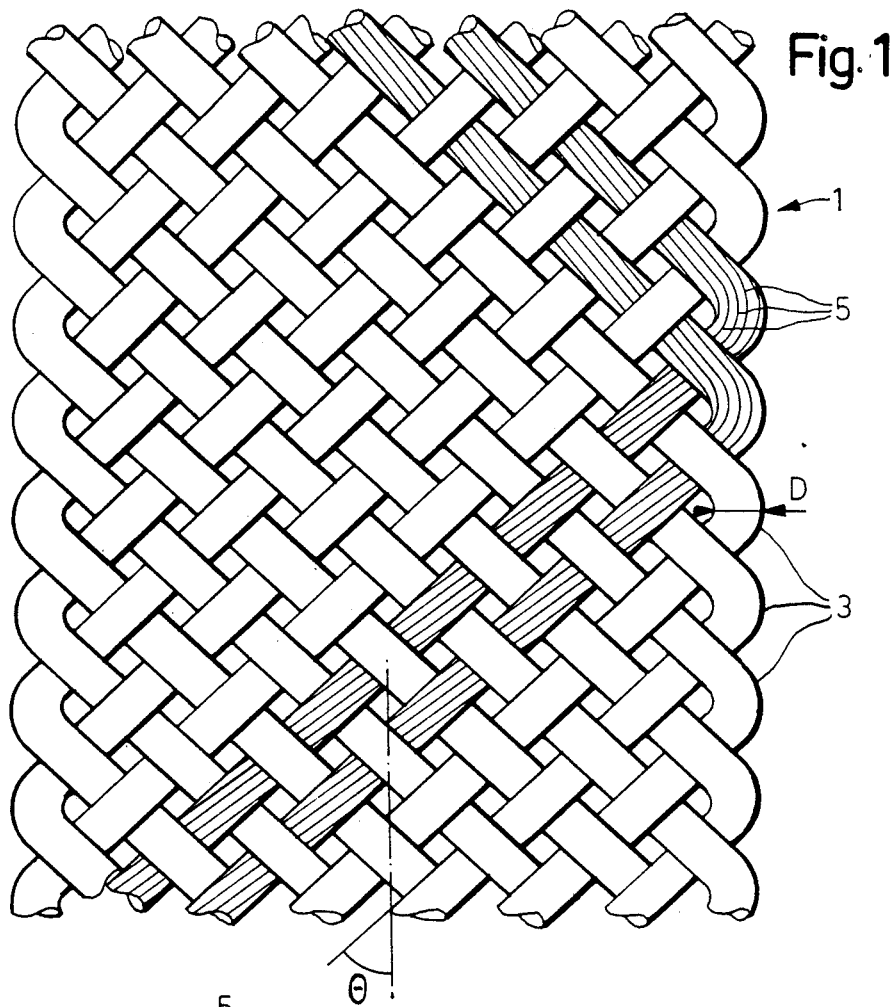
FIG. 1 a plan view of an alloplastic material plaited into a plane strap.

The alloplastic material 1 shown in FIG. 1 consists of an areal, single-layer strap and comprises a number of loosely interconnected mutually plaited bundles 3. Each bundle runs zigzag- or wave-shaped within a plane, the bundles being mutually connected at regular intervals over their entire length by the plaited formation. Each bundle 3 consists of fibers 5 loosely held together. In FIG. 1, the fibers 5 are shown only in two of the bundles, also the number of fibers is in reality substantially larger than shown in the drawing. Each fiber comprises at least one metallic material, namely titanium or a titanium-based alloy.

Figure 2:
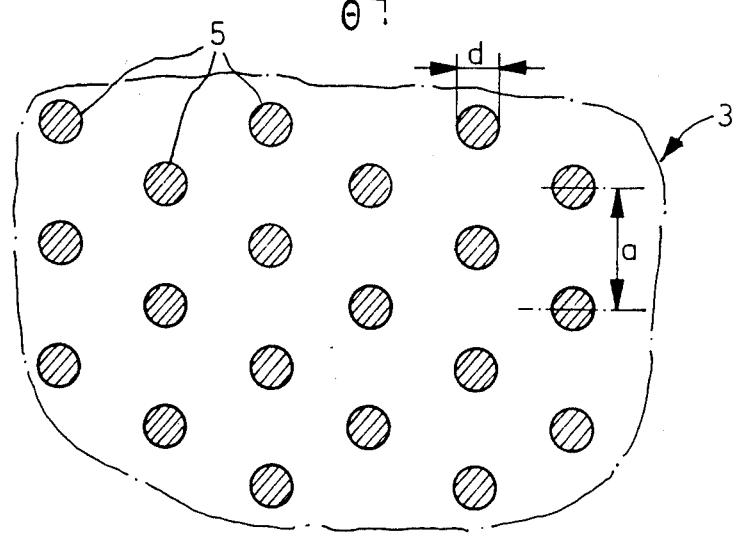
FIG. 2 a schematic cross-section through part of a bundle of fibers drawn to a larger scale, FIG. 3 a schematic end view of a hose-shaped alloplastic material, FIG. 4 a schematic view of an alloplastic material comprising a helix-shaped bundle of fibers, and FIG. 5 a schematic view of an alloplastic material comprising a zigzag- or wave-shaped bundle of fibers.

The bundles 3 form a plaiting angle $\theta$ of 45° with the longitudinal direction of the strap, and have a substantially circular cross-section of a diameter D. The fibers 5 are of circular cross-section of diameter d, as shown in FIG. 2. The fibers 5 of a bundle 3 are loosely twisted together, so that, in general, clearance spaces exist between adjacent fibers. However, the fibers may come in contact with each other in pairs or in groups in certain places, for example in places in which the bundles 3 are greatly curved, such as at the longitudinal edges of the strap. The fibers 5 are thus given the possibility to move relative to each other, generally transversely with respect to the longitudinal direction of the fibers and bundles, at least in the relaxed, unstressed state of the strap. Since the bundles 3 follow a bent or curved path, the loose structure of the fiber formation enables longitudinal sections of the fibers 5 to also move, within certain limits, relative to each other, in longitudinal direction of the fibers.

The distances between fibers nearest to each other may vary from place to place and from fiber to fiber. To be able to explain a few variables and notations it will now be assumed, that the distance between fibers nearest to each other has the value a for all fibers, this value to be interpreted, to advantage, as a mean value averaged in a suitable manner. The distance a must evidently be larger than the diameter d of the fibers. While drawing the FIG. 2 it was assumed that the fibers 5 are distributed, in a cross-section running transversely to the respective bundle 3, in a two-dimensional, regular, hexagonal lattice, and are located in the corners and the centers of continuously interconnected hexagons of uniform sizes. The average distance denoted by a, of the fibers nearest to each other is thus equal to the length of the side of a hexagon. If the assumption is made, that the fibers define a hexagonal lattice as illustrated in FIG. 2, and the ratio V is to have the value $V_{hex}$, where 'hex' stands for hexagon, then $$V = V_{hex} = 0.906 \, d^2/a^2 \qquad (3)$$

The fibers could also define, in places, a two-dimensional square lattice, i.e. they could be located within a cross-section lying transversely to the direction of the bundles, in the corners of continuously interconnected squares of uniform sizes. In this case, the ratio V would have the value $V_{sq}$, where 'sq' stands for square, and $$V = V_{sq} = 0.785 \, d^2/a^2 \qquad (4)$$

Thus if, for example, the diameter d and the ratio V are preselected, then the approximate value of the average distance a may be calculated or at least estimated using the formulas (3) and (4). In the case of FIG. 2, the ratio V has a value of about 0.1, and d/a correspondingly a value of about 0.3.

The alloplastic material 1 may be made by first producing bundles of fibers in accordance with the method described in the introduction, by subsequently twisting the bundles around, i.e. winding them around the longitudinal axis of the bundle, and by mutually plaiting the desired number of bundles. Instead, it is possible to twist the previously stretched composite wires containing a matrix consisting for example of copper, in addition to the fibers, and to mutually plait them, and to dissolve the matrix by means of an acid after the plaiting has been accomplished. Furthermore, the fiber bundles may be coated before or after being plaited and subsequent to dissolving the matrix, with an organic substance that may be absorbed later inside the body. This substance will then enclose the individual fibers, with the exception of those fiber sections that may be in direct contact with each other, there being no clearance spaces therebetween. As an alternative, the twisting or winding of the fibers of a bundle could be dispensed with, and instead the fibers of a bundle could run more or less parallel to the longitudinal axis of the bundle. Subsequent to plaiting the bundles, the fibers of the bundle will be held together by the plaited formation. If the fibers are made of a titanium alloy of the beta-type, their mechanical strength properties may be additionally improved by solution annealing and/or by aging, either before or after the fiber bundles have been plaited.

In order to make an artificial ligament or an artificial tendon, the strap-shaped alloplastic material 1 may be fastened with its ends on bones, when inserted into the body. To this effect, holes may be drilled into the bones and the fiber formation clamped fast on pins inserted into the holes, the pins too consisting of bone material. The natural, rigid bone material may then, in analogy to the soft tissue, grow to a certain extent onto the metallic fibers.

Tests were carried out producing rough blanks comprising 1800 wires made of a TiNb-alloy of the beta-type and containing 40% by weight niobium and the rest titanium, the wires being imbedded into a matrix of copper. The rough blanks were converted by hot-pressing and cold-drawing, into composite wires having diameters of 0.8 mm, and lengths between 10 and 15 m, these lengths being subsequently cut to the desired lengths. The fibers remaining after the copper matrix has been dissolved, had diameters between 12 and 13 micrometers. The fibers present in a bundle thus had a total cross-sectional area of about 0.22 mm². The tensile strength of the bundles were between 150 and 200 N per bundle. An alloplastic material was constructed by plaiting 18 bundles together to form a strap having a tensile strength of about 3 kN. This is significantly higher than the tearing stress of a natural knee-ligament.

In analogous manner were constructed fiber bundles of an alloy of the beta-type containing 15% by weight molybdenum, 5% by weight zirconium, 3% by weight aluminum and the rest titanium. This alloy is similar to the TiNb-alloy in showing good deformability without any disturbing stiffening effects. The fiber bundles were subjected, before dissolving the matrix, to a heat treatment at about 500° C. Tearing tests yielded ultimate stress values as high as 1.4 GPa.

If an alloplastic material to serve as artificial ligament or as artificial tendon is implanted into the body, there will form, after a certain amount of time, a matrix of natural soft tissue interpenetrating the fibers 5, enclosing the same and adhering to them. This soft tissue will be equally stretched when the fiber formation 1 is stretched, while the forces will become distributed onto the fiber formation 1 and the natural soft tissue. When the length of an individual piece of fiber on which natural soft tissue has adhered is at least equal to the critical tear-out length L defined in the introduction, then the shearing force required for shearing the natural soft tissue off the fibers, is larger than the fracture stress of the fiber when subjected to tension. According to formula (2), the critical tear-out length of fibers made of the named titanium-niobium-alloy and having diameters between 12 and 13 micrometers lies between 0.6 and 1 mm. This is, compared to the length of common ligaments and tendons, too short, so that the natural soft tissue, as soon as it has grown into a short part of the alloplastic material, will be able to compensate for unequal stresses in the fibers and, if a fracture occurs in one fiber, it will be able to transfer the force transmitted by the respective fiber, onto the neighbouring fibers. If the ratio V, i.e. the share of the total cross-sectional area of the fibers 5 of a bundle 3 in the total cross-sectional area of the bundle grown into by natural tissue, has a value of 0.1 for example, so that a ratio approximately corresponding to the ratio shown in FIG. 2 will result between the distances a of adjacent fibers and the diameters d, and the distances a will be on the average about 0.04 mm, then, on the one side, the distances a will still be substantially smaller than the critical tear-out length L, thus making possible a good transmission of force, and, on the other side, the volume of the additionally grown natural tissue will be large enough, to enable this tissue to fulfill the full function, so to speak, of a ligament or a tendon.

The embodiment of the alloplastic material 11 illustrated in FIG. 3 comprises a number of fiber bundles 3, the individual bundles being mutually plaited to form a hose. The plait is preferably constructed to have all of the bundles 3 form helices running around the longitudinal axis of the hose with identical pitch, one half of the bundles being arranged to run like a right-handed screw-thread and the other half like a left-handed screw-thread.

The alloplastic material 21 shown in FIG. 4 also comprises at least one helix-shaped bundle 3 of, for example, slightly twisted fibers. However, in this case the bundle 3 is not plaited with any other bundle, but may be connected at its ends with other bundles, by means of fastening members not shown in the drawing, and is thus left free over the largest part of its length. The pitch S is larger than the average diameter $D_w$ of the helix and, for example, has a value of approximately 6 $D_w$ or less.

The alloplastic material 31 shown in FIG. 5 comprises a fiber bundle 3 that runs zigzag-, and/or wave-shaped within a plane. The wave-length $L_w$ is larger than the wave height H of the bundle, as measured between center axes of the bundle, and has a value of approximately 4H or less. If several bundles are provided, these should be connected, at the utmost, at their ends, by way of common fastening members.

The helix- or wave-shaped bundle according to the FIGS. 4 or 5, respectively, may be manufactured by subjecting a bundle of wires of titanium or a titanium alloy imbedded into a matrix, to deformation, in the manner described in the introduction, until the wires acquire the desired diameters. The composite wire resulting in this way may then be formed into a helix-shape or a wave-shape, as the case may be. The matrix may then be dissolved by means of an acid.

While there are shown and described present preferred embodiments of the invention, it is to be distinctly understood that the invention is not limited thereto but may be otherwise variously embodied and practiced within the scope of the appended claims.

What is claimed is:

1. Alloplastic material for making at least one of an artificial soft tissue component and a reinforcement for a natural soft tissue component in a human or animal body, wherein the material comprises fibers of a thickness less than 20 micrometers, the fibers contain an alloy having a phase structure of one of alpha-beta type and beta type and said fibers arranged in a regular pattern.

2. Material as claimed in claim 1, wherein the alloy comprises titanium.

3. Material as claimed in claim 1, wherein titanium is the metallic component of largest percentage by weight in the alloy.

4. Material as claimed in claim 1, wherein titanium represents at least 50% by weight of the alloy.

5. Material as claimed in claim 4, wherein the alloy also contains at least one of the metals niobium, tantalum, zirconium, chromium, molybdenum, iron and aluminum.

6. Material as claimed in claim 1, wherein the fibers are arranged to form at least one bundle having at least 100 fibers, the fibers of a bundle being loosely held together, with clearance spaces therebetween to enable natural body tissue to grow into the alloplastic material implanted into a human or animal body, in the clearance spaces between adjacent fibers.

7. Material as claimed in claim 6, wherein the fibers are coated at least in part with a substance which when implanted into a human or animal body is absorbed by the respective body.

8. Material as claimed in claim 7, wherein the coating substance is collagen, polyglactin, polylactate or gelatine.

9. Material as claimed in claim 6, the bundle comprises at least 200 fibers.

10. Material as claimed in claim 6 wherein the bundle comprises at least 1000 fibers.

11. Material as claimed in claim 6, wherein the bundle is zigzag-shaped.

12. Material as claimed in claim 6, comprising at least two or more bundles loosely connected with each other.

13. Material as claimed in claim 6, comprising at least two bundles disposed adjacent to each other and fastened at ends thereof to common members, and being free between the ends thereof.

14. Material as claimed in claim 6, wherein the fibers belong to a bundle with a longitudinal axis and are arranged to run parallel to the longitudinal axis.

15. Material as claimed in claim 1, wherein the fibers have a relaxed state and are arranged to enable the material, starting out from the relaxes state, to be stretched in at least one direction by at least 5% of the running direction of the fibers during such stretching being subject to change.

16. Material as claimed in claim 1, wherein the fibers have a relaxed state and are arranged to enable the material, starting out from the relaxes state, to be stretched in at least one direction by at least 10% of the running direction of the fibers during such stretching being subject to change.

17. Material as claimed in claim 1, wherein the fibers are cold-formed.

18. Material as claimed in claim 17, wherein the fibers are heat-treated after being cold-formed.

19. Material as claimed in claim 1, wherein the fibers are not greater than 15 micrometers thick.

20. Alloplastic material for making at least one of an artificial soft tissue component and a reinforcement for a soft tissue component in a human or animal body, wherein the material comprises at least one bundle comprising at least 100 fibers comprising an alloy, each fiber having a thickness less than 20 micrometers thick, said fibers in said bundle being loosely held together to enable natural body tissue to grow into the alloplastic material in clearance spaces between adjacent fibers.

21. Material as claimed in claim 20, wherein said bundle comprises at least 200 fibers.

22. Material as claimed in claim 20, wherein the bundle comprises at least 1,000 fibers.

23. Material as claimed in claim 20, wherein at least two said bundles are loosely connected with one another.

24. Material as claimed in claim 20, wherein said alloy having a phase structure of one of alpha-beta type and beta type.

25. Material as claimed in claim 24, wherein titanium is a metallic component having the largest percentage by weight in the alloy.

26. Material as claimed in claim 25, wherein said titanium comprises at least 50% by weight of the alloy.

27. Material as claimed in claim 26, wherein the alloy of the fibers contains at least one of the group of metals comprising niobium, tantalum, zirconium, chromium, molybdenum, iron and aluminum.

28. Alloplastic material for making at least one of an artificial soft tissue component and a reinforcement for a soft tissue component in a human or animal body, wherein the material comprises at least one bundle having at least 100 fibers, each said fiber being less than 20 micrometers thick and comprising an alloy having a phase structure of the beta type, said alloy comprises titanium as a metallic component of the greatest percentage by weight, said fibers in said bundle being loosely held together for enabling natural body tissue to grow into clearance spaces between adjacent fibers in the alloplastic material.

29. Material as claimed in claim 28, wherein the alloy includes niobium.

30. Material as claimed in claim 28, wherein said fibers are cold-formed.

31. Material as claimed in claim 28, wherein at least two said bundles are loosely connected.

32. Material as claimed in claim 28, wherein several bundles are plaited into a planar single-layer strap.

* * * * *